(12) United States Patent
Bouvier et al.

(10) Patent No.: US 7,932,080 B2
(45) Date of Patent: Apr. 26, 2011

(54) DOUBLE BRILLIANCE BETA-ARRESTIN: A BIOSENSOR FOR MONITORING THE ACTIVITY OF RECEPTORS AND SIGNALLING MOLECULES, AND METHOD OF USING SAME

(75) Inventors: Michel Bouvier, Montreal (CA); Pascale Charest, San Diego, CA (US)

(73) Assignee: Valorisation-Recherche, Limited Partnership, Montreal, Quebec (CA)

( * ) Notice: Subject to any disclaimer, the term of this patent is extended or adjusted under 35 U.S.C. 154(b) by 344 days.

(21) Appl. No.: 11/579,482

(22) PCT Filed: May 4, 2005

(86) PCT No.: PCT/CA2005/000695
§ 371 (c)(1),
(2), (4) Date: Apr. 28, 2008

(87) PCT Pub. No.: WO2005/105850
PCT Pub. Date: Nov. 10, 2005

(65) Prior Publication Data
US 2009/0123953 A1 May 14, 2009

(51) Int. Cl.
*C12M 1/34* (2006.01)
(52) U.S. Cl. .................................... 435/287.1
(58) Field of Classification Search .................. None
See application file for complete search history.

(56) References Cited

FOREIGN PATENT DOCUMENTS
CA        2335305        12/1999

OTHER PUBLICATIONS

Scott et al. "Differential nucleocytoplasmic shuttling of beta-arrestins", JBC, 2002, 277(40):37693-37701.*
Xu et al., "A bioluminescence Resonance Energy Transfer (BRET) System: Application to Interacting Circadian Clock Proteins," Jan. 1999. Proceedings of National Academy of Sciences, vol. 96, pp. 151-156.
Oakley et al., "Molecular Determinants Underlying the Formation of Stable Intracellular G Protein-coupled Receptor Beta-Arrestin Complexes after Receptor Endocytosis," Jun. 2001, Pub JBC Papers in Press Mar. 9, 2001, Journal of Biological Chemistry, vol. 276, No. 22, pp. 19452-19460.
Barak et al., "A Beta-arrestin/Green Fluorescent Protein Biosensor for Detecting G Protein-coupled Receptor Activation," Oct. 1997, Journal of Biological Chemistry, vol. 272, No. 44, pp. 27497-27500.
International Search Report corresponding to PCT/CA2005/000695, under date of mailing of Aug. 25, 2005.
Angers S, et al., "Detection of Beta2-adrenergic Receptor Dimerization in Living Cells Using Bioluminescence Resonance Energy Transfer (BRET)", Proceedings of the National Academy of Sciences, Mar. 2000, vol. 97, No. 7, pp. 3684-3689.
Bertrand L. et al., "The BRET2/arrestin Assay in stable Recombinant Cells: A Platform to Screen for Compounds that Interact with G Protein-Coupled Receptors (GPCRs)", Journal of Receptors and Signal Transduction, Feb.-Nov. 2002, vol. 22, No. 1-4, pp. 533-541.
Kroeger KM, et al., "Constitutive and Agonist-dependent Homo-oligomerization of the Thyrotrophin-releasing Hormone Receptor," Journal of Biological Chemistry, Apr. 2001, vol. 276, pp. 12736-12743.
Charest PR, et al., "Monitoring Agonist-Promoted Conformational Changes of Beta-arrestin in Living Cells by Intramolecular BRET," EMBO Reports, Apr. 2005, pp. 334-340.

* cited by examiner

*Primary Examiner* — Karen Cochrane Carlson
*Assistant Examiner* — Bin Shen
(74) *Attorney, Agent, or Firm* — Quarles & Brady LLP

(57) ABSTRACT

An intramolecular bioluminescence resonance energy transfer (BRET), biosensor for monitoring receptor activity and signalling cascades is disclosed. The "double-brilliance" biosensor sandwiches β-arrestin (β-arr) between *Renilla* luciferase (Luc) and the yellow fluorescent protein (YFP). β-arr associates with G-protein coupled receptors GPCR following receptor activation, bringing Luc and YPF into close proximity that favours energy transfer. In addition to providing new insights into the agonist-induced conformational rearrangements of β-arr in living cells, the double-brilliance β-arr offers a universal biosensor for GPCR activation, allowing the study of native receptors in large-scale screening analysis. The activity of other signalling molecules known to interact with β arrestin could also be monitored by double brilliance β arr.

27 Claims, 11 Drawing Sheets

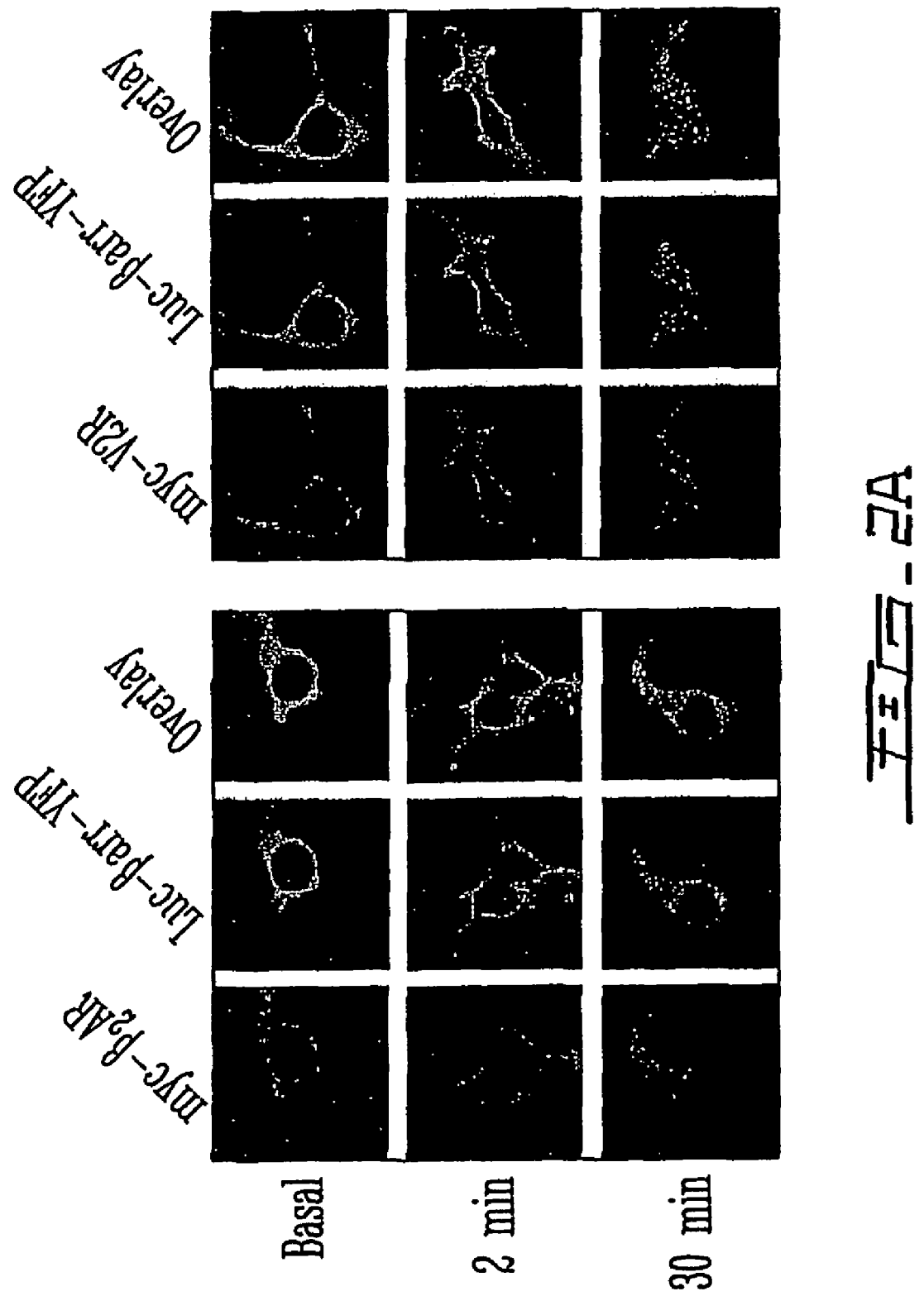
FIG_2A

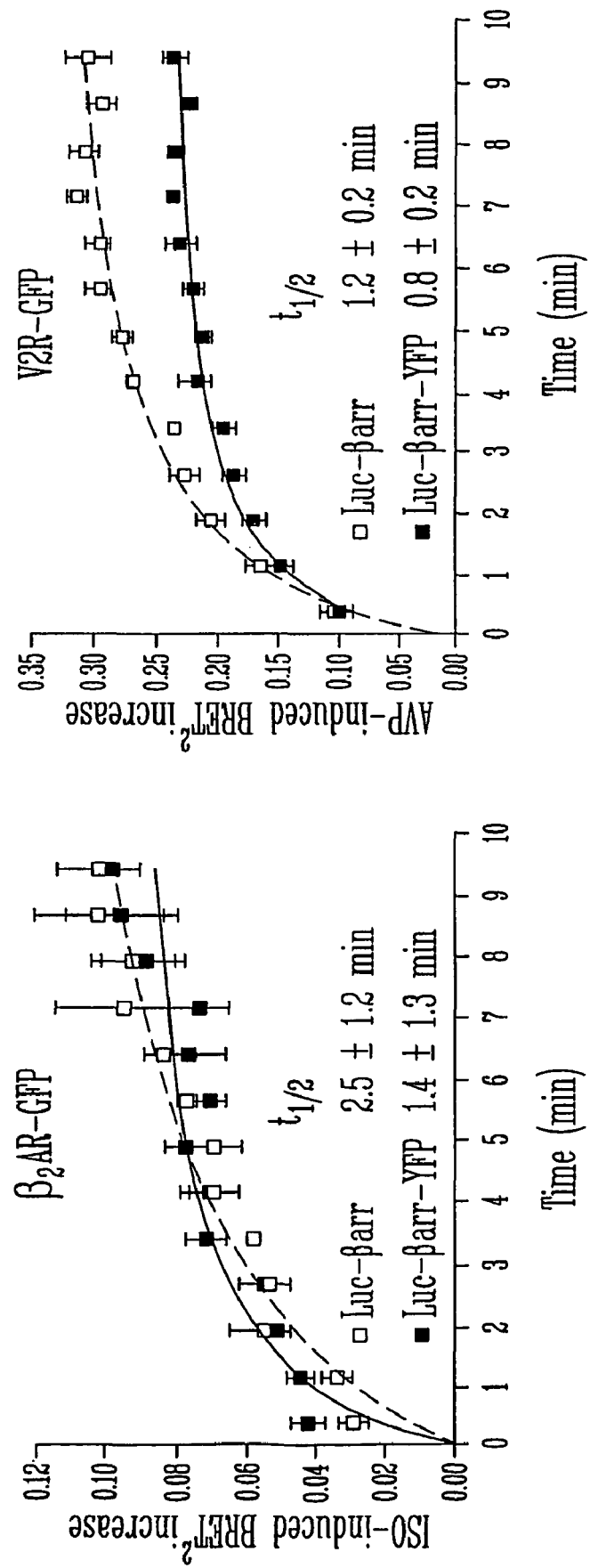

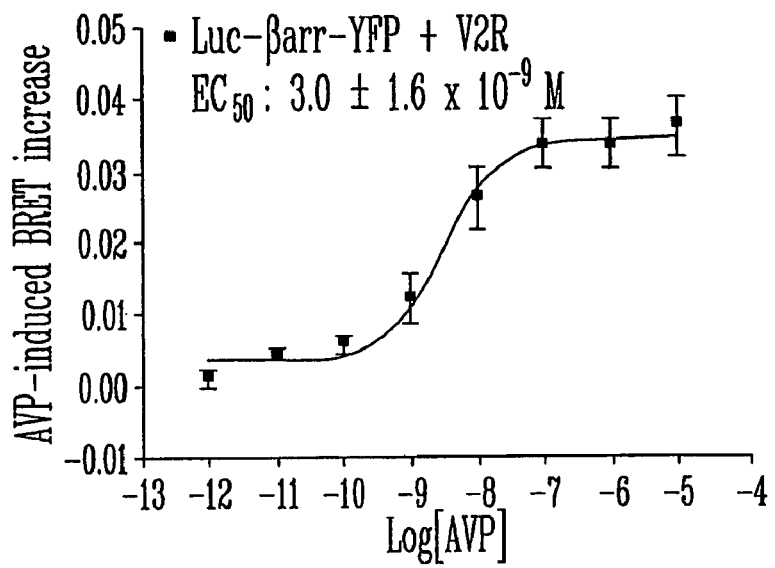
FIG_3C
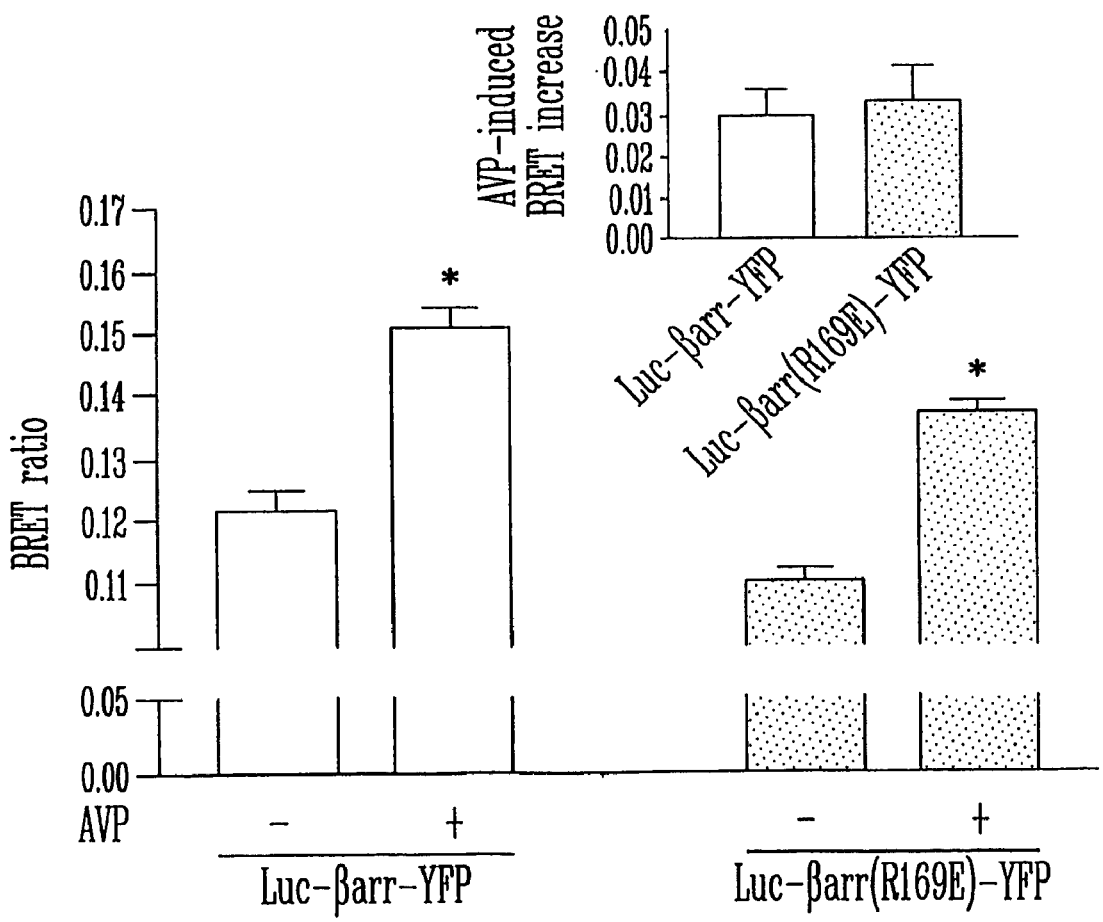
FIG_4

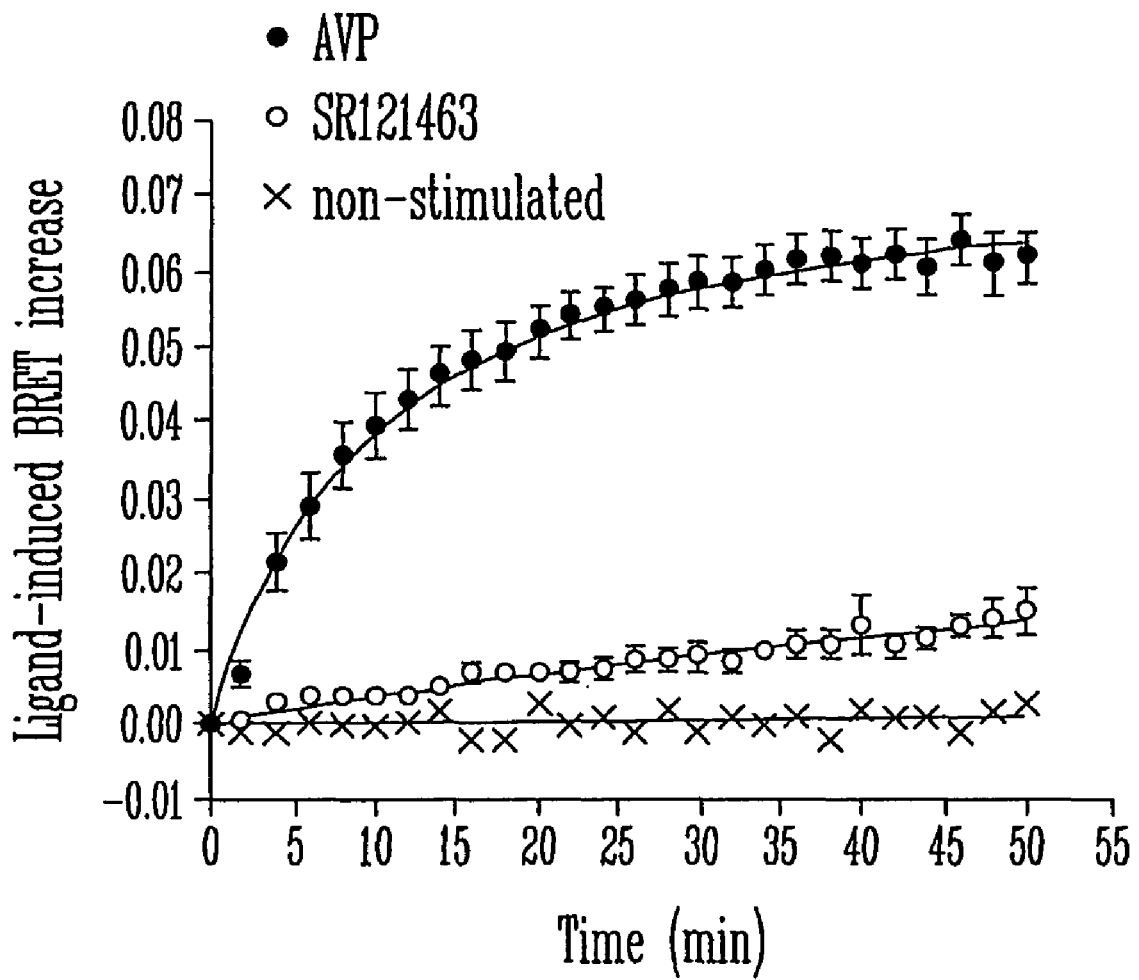
FIG_7

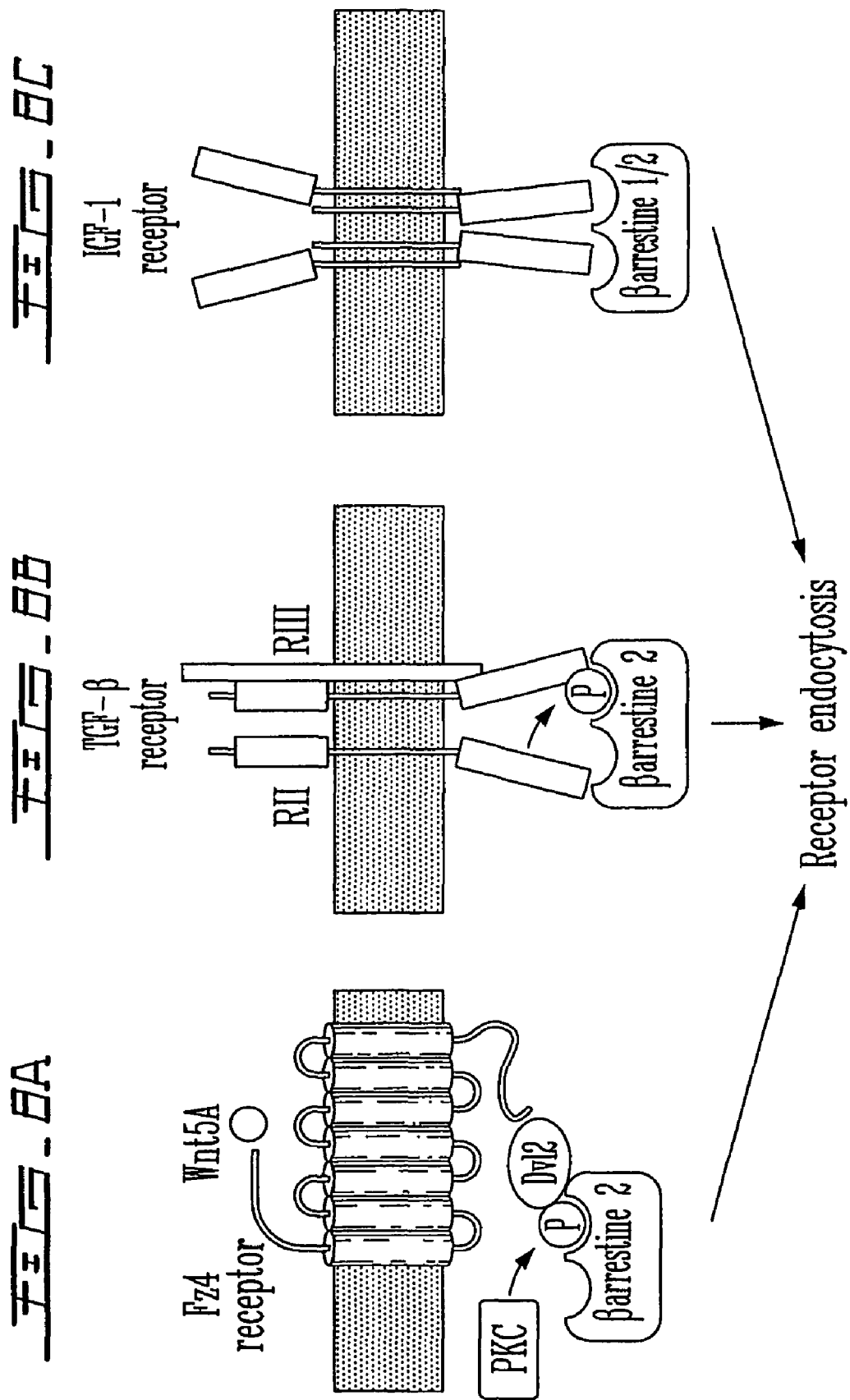

DOUBLE BRILLIANCE BETA-ARRESTIN: A BIOSENSOR FOR MONITORING THE ACTIVITY OF RECEPTORS AND SIGNALLING MOLECULES, AND METHOD OF USING SAME

TECHNICAL FIELD

The invention relates to a novel biosensor and method which are suitable to monitor activation of receptors and signalling molecules. More specifically, the invention concerns the use of a modified arrestin as a biosensor to monitor the activation state of protein-coupled receptors, such as G protein-coupled receptors (GPCR). Advantageously, the biosensor and method of the present invention allow for a highly sensitive and quantitative assay that can be used in large-scale screening analyses.

BACKGROUND OF THE INVENTION

G-protein-coupled receptors (GPCRs) relay the information provided by numerous hormones and neurotransmitters into intracellular signalling pathways, primarily through their coupling to heterotrimeric G proteins. Agonist stimulation of GPCRs also initiates their feedback desensitization, mostly mediated by GPCR kinases (GRKs) and β-arrestin (β-arr) proteins. Through their binding to agonist-occupied, GRK-phosphorylated receptors, β-arrs prevent further coupling to G proteins and promote GPCR endocytosis, thus leading to decreased signalling efficacy. In addition to their role in receptor desensitization, β-arrs can act as scaffolds, linking GPCRs to mitogen-activated protein kinase signalling pathways (Luttrell & Lefkowitz, 2002). When considering their interaction with β-arrs, GPCRs can be divided into two classes: class A receptors interact only transiently with β-arr and undergo efficient recycling when released from β-arr, whereas class B receptors stably associate with β-arr as a result of higher affinity, thus leading to the accumulation of intracellular receptor/β-arr complexes that prevent receptor recycling (Oakley et al, 2001). Solved crystal structures (Hirsch et al, 1999; Han et al, 2001), mutagenesis (Vishnivetskiy et al, 2002) and limited tryptic proteolysis studies (Gurevich & Benovic, 1993; Xiao et al, 2004) suggest that a conformational rearrangement of the β-arr molecule accompanies its interaction with the activated receptor. It has been proposed that known intramolecular interactions between the amino- and carboxy-terminal domains in the inactive state are modified in the active β-arr, suggesting that the domains move relative to each other on activation. In this process, the C-tail seems to be released, thus exposing its clathrin—and adaptin 2 (AP2)—binding sites and promoting interactions with the internalization machinery (Lin et al, 1999, 2002; Gurevich & Gurevich, 2003).

In addition to their interactions with GPCRs, β-arrs were recently found to interact with receptors of other classes including receptor tyrosine kinases, receptor serine and threonine kinases, as well as adaptor proteins such as Disheveled (Lefkowitz and Whalen 2004) indicating that βarrs could be sensing the activated states of a wide diversity of signalling molecules.

Despite the growing diversity in GPCR signalling mechanisms, definitions of drug efficacy are often linked to a scheme considering only the regulation of the classical G protein signalling. Within this framework, agonists are defined as drugs that stabilize an active receptor conformation that induces G protein activation, whereas inverse agonists favor an inactive receptor state that reduces spontaneous G protein signalling. The question arises as to whether this paradigm may be transferred to drug effects generated through the formation of metastable complexes involving scaffolding proteins such as β-arr. Because all studies describing β-arr-mediated MAPK signalling have concentrated on agonist drugs, little is known of how ligands that are commonly classified as inverse agonists may regulate the scaffold assembly that is crucial for such signalling.

In one study (Azzi et al, 2003), this question was addressed by assessing whether $\beta_2$-adrenergic receptor ($\beta_2$AR) and V2 vasopressin receptor (V2R) ligands with proven inverse efficacy on adenylyl cyclase (AC) activity could also regulate MAPK activation via receptor-mediated scaffold formation. It was found that, despite being inverse agonists in the AC pathway, the β2AR (ICI118551 and propranolol) and V2R (SR121463A) induced the recruitment of β-arr leading to the activation of the ERK cascade. Such observations indicate that the same drug acting on a unique receptor can have opposite efficacies depending on the signalling pathway considered.

The above study relied on the use of a bimolecular bioluminescence resonance energy transfer (BRET) assay. It was used to assess β-arrestin recruitment to $\beta_2$AR or V2R. Fusion proteins consisting of GFP10 variant (GFP) covalently attached to the carboxyl tail of the receptor of interest ($\beta_2$AR-GFP; V2R-GFP) were co-expressed with β-arrestin 2 fused at its carboxyl terminus to Rluc (β-arrestin-Rluc). After incubation of the transfected cells with different ligands, Deep Blue coelanterazine (Packard) was added and readings were collected using a modified top-count apparatus (BRETCount, Packard) that allows the sequential integration of the signals detected at 370-450 nm and 500-530 nm. The BRET signal was determined by calculating the ratio of the light emitted by the Receptor-GFP (500-530 nm) over the light emitted by the β-arrestin-2-Rluc (370-450 nm). The values were corrected by subtracting the background signal detected when the β-arrestin-2-Rluc construct was expressed alone.

While the results elicited from the above study were instructive, a necessary feature involved the construction of fusion proteins that included the receptors of interest. Ideally, a method could be devised in which receptor activation might be observed without first having to modify the receptors that are to be studied. Other features of such a method that would make it highly desirable for research and development endeavors include the following: (1) a high level of sensitivity; (2) an ability to provide quantitative results; (3) adaptability for use in large scale screening analyses; (4) an assay that requires the expression of a single recombinant constructs; and (5) a biosensor based on an intramolecular BRET signal.

There is a need, therefore, for a simpler method to measure receptor activity in living cells. The present invention seeks to meet this and related needs.

SUMMARY OF THE INVENTION

In accordance with the present invention, a novel biosensor and method are provided which are suitable to monitor activation of receptors and signalling molecules, such as G protein-coupled receptors.

As indicated above, βarr recruitment to activated GPCR promotes a conformational change in βarr. To assess whether such agonist-promoted conformational changes of β-arr occur in living cells and to obtain further information on the relative positions of the C- and N-terminal domains during the activation process, an intramolecular bioluminescence resonance energy transfer (BRET)-based biosensor was devised. This biosensor consists of a β-arr molecule sandwiched between the bioluminescent donor *Renilla* luciferase (Luc) and the yellow fluorescent protein (YFP). Using this double-brilliance β-arr biosensor (Luc-β-arr-YFP), it is possible to show that β-arr undergoes important conformational rearrangement after agonist stimulation, where the N terminus and C terminus are brought in closer proximity and/or into an orientation that favors resonance energy transfer.

Comparison of the kinetics of β-arr recruitment to the receptors and its conformational change indicates that the latter follows the initial recruitment of β-arr to agonist-activated receptors. In addition to providing new insights into the structural rearrangements following β-arr activation in living cells, the above demonstrates the utility of double-brilliance β-arr as a general biosensor of GPCR activity that could be used in large scale or high throughput screening of GPCR ligands. Since β-arr has also been shown to interact with other classes of activators, receptors and signalling molecules, the method and biosensor described herein could become a general tool for different classes of molecules, including tyrosine kinase receptors, serine and threonine kinase receptors and accessory proteins such as Disheveled.

Other objects, advantages and features of the present invention will become more apparent upon reading of the following non restrictive description of preferred embodiments thereof, given by way of example only with reference to the accompanying figures.

BRIEF DESCRIPTION OF THE FIGURES

FIG. 4: Agonist-promoted conformational change of a phosphate insensitive βarrestin mutant. HEK293 cells were transfected with V2R and either Luc-βarr-YFP or Luc-βarr (R169E)-YFP. Cells were stimulated or not for 10 min with 1 µM AVP prior the addition of 5 µM coelanterazine h (Molecular Probe) and performing the intramolecular BRET1 measurements using a Multilabel Reader Mithras LB 940 (Berthold Technologies). The BRET signal was determined by calculating the ratio of the light emitted by YFP over the light emitted by Luc following the addition of coelenterazine h. The values were corrected by subtracting the background BRET signals detected when Luc-βarr was expressed alone. Inset, AVP-induced BRET increase. Data represent the mean±SEM of three independent experiments. * indicates $p<0.02$ between treatment and each individual control condition.

FIG. 6: Agonist-promoted conformational change of constitutively activated βarrestin mutants. HEK293 cells were transfected with V2R and either Luc-βarr-YFP or Luc-βarr (3A)-YFP or Luc-βarr (IV)-YFP. Cells were stimulated or not for 10 min with 1 µM AVP prior to the addition of 5 µM coelanterazine h and performing the BRET measurements as described in the previous figure. Inset, AVP-induced BRET increase. The BRET signal was determined by calculating the ratio of the light emitted by YFP over the light emitted by Luc following the addition of coelenterazine h. The values were corrected by subtracting the background BRET signals detected when Luc-βarr was expressed alone. Data represent the mean±SEM of two independent experiments. * indicates $p<0.05$ between treatment and each individual control condition.

FIG. 7: Conformational change of βarrestin induced by ligands of different efficacies. HEK293 cells transiently co-expressing the V2R and Luc-βarr-YFP were subjected to real time BRET measurements in the presence or absence of two different V2R ligands. The basal BRET signals were subtracted from each condition to express the data as ligand-induced BRET increase. The figure shows the detection of conformational changes of Luc-βarr-YFP in time, reflected by the increase in BRET signal, induced by the V2R agonist AVP or the inverse agonist SR121463. No BRET increase is observed when cells were incubated in the presence of the carrier alone (non-stimulated). The fact that the observed increase in BRET signal induced by SR121463 is significantly lower than that induced by AVP treatment can be correlated with the smaller SR121463-mediated recruitment of βarrestin to the V2R when compared to AVP, as reported previously (Azzi et al, 2003).

DETAILED DESCRIPTION OF THE INVENTION

Definitions

Figure 1:
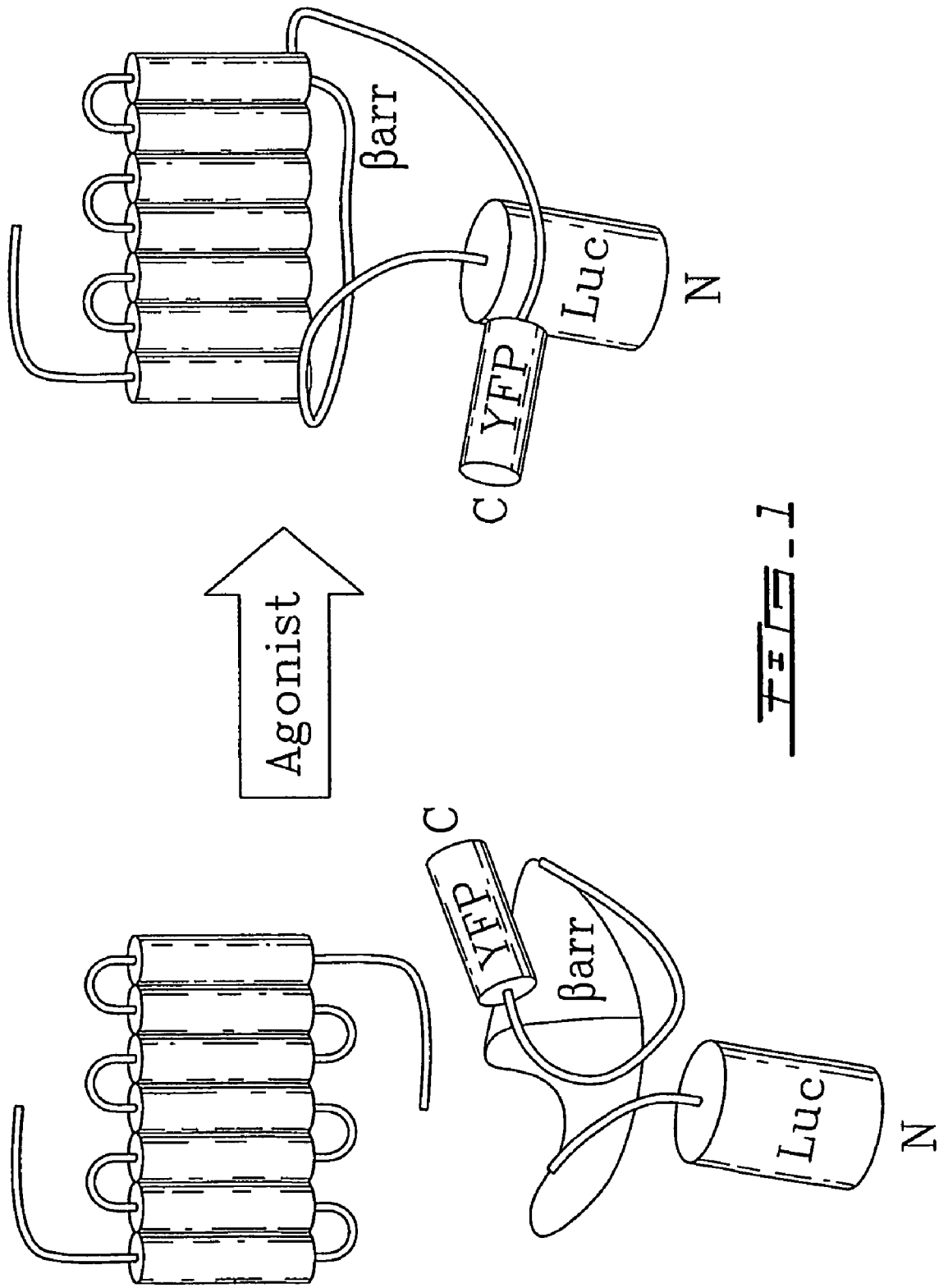
FIG. 1: Double-brilliance β-arr. Schematic diagram illustrating how agonist-promoted conformational rearrangement of β-arr can be measured as changes in BRET using double-brilliance β-arr. Luc and YFP are represented by cylinders proportional to their sizes, but their real orientation is unknown.

Unless otherwise defined, the terms used in the present description have the meanings that would be understood by a person of skill in the art.

Ligand: A molecule which may be but is not restricted to a hormone, neurotransmitor, chemical compound, drug, or diagnostic agent, that binds to a receptor and has an agonistic, inverse agonistic, antagonistic or allosteric effect on the receptor.

Agonist: a ligand that has the same or similar effect as a hormone, neurotransmitter or signalling molecule or a group of hormones, neurotransmitters or signalling molecules activating a receptor.

Allosteric regulator: a ligand that modulates receptor activity through binding at a site that is different from that bound by agonists, inverse agonists or antagonists.

Antagonist: a ligand that counteracts the effect of another ligand or group of ligands acting on a receptor.

Inverse agonist: a ligand that produces an effect opposite to that of an agonist by occupying the same receptor.

Partial agonist: a ligand with lower intrinsic activity than a full agonist and that produces a lower maximum effect.

Beta(β)-arrestin: A protein that is recruited to activated receptors or signaling molecules and is involved in modulating receptor's ability to activate G proteins. It also acts as a scaffold to activate the MAPK signalling pathway and promotes receptor endocytosis. Two isoforms of βarrestins known as βarrestin1 and βarrestin2 exist.

Bioluminescence Resonance Energy Transfer (BRET) Assay: a proximity assay based on the nonradiative transfer of energy between a donor luminescent enzyme (ex: luciferase) and a fluorophore (ex: GFP or YFP).

Fluorescence Resonance Energy Transfer (FRET) Assay: similar to BRET, it involves the transfer of energy from an excited donor fluorophore to an adjacent acceptor fluorophore. For example, CFP and YFP, two color variants of GFP, can be used as donor and acceptor.

BRET1: uses coelenterazine h as the luciferase substrate and YFP and its variants as the energy acceptor.

BRET2: uses DeepBlueC™ coelenterazine (Perkin-Elmer, Wellesley, Mass., USA) as the luciferase substrate and GFP2 or GFP10 as the energy acceptor.

Biosensor: A type of biomolecular probe that measures the presence or concentration of biological molecules, biological structures, activity state etc., by translating a biochemical interaction at the probe surface into a quantifiable physical signal such as light or electric pulse.

Fluorophore: A small molecule, or a part of a larger molecule, that can be excited by light to emit fluorescence. Fluorescence is emitted when a fluorophore interacts with an incident photon.

Variant: A molecule or protein which is substantially similar in structure and biological activity to the molecule or protein of the present invention.

YFP, GFP-2 and GFP-10: Variants of the green fluorescent protein that can be used in BRET assays, including YFP, Venus, Topaz, GFP2 and GFP10.

Luciferase: *Renilla* luciferase is a luminescent enzyme that emits light upon oxydation of its substrate (ex: coelenterazine).

Receptor: A popular and generally accepted hypothesis that appears to explain many pharmacodynamic phenomena holds that specialized protein molecules on the surfaces of cells provide a "fit" for an intrinsic molecule (such as a hormone or neurotransmitter) or a drug such that when that molecule occupies (binds to) that area, it leads to a biochemical or physiologic response. This idea is often compared to the operation of a lock (receptor) by a key (ligand).

Signalling molecule: a membrane or soluble protein involved in the transaction of signals in cells initiated by hormones, neurotransmitters or synthetic ligands.

Specific Agonists angiotensin II: The active form of angiotensin. An octapeptide found in blood, it is synthesised from angiotensin I and quickly destroyed. Angiotensin II causes profound vasoconstriction with resulting increase in blood pressure. It is an agonist of the angiotensin receptor.

AVP: arginine vasopressin, vasopressin containing arginine, as that from most mammals, including man. This hormone controls water reabsorbtion by the kidney and is also known as the antidiuretic hormone.

ISO: isoproterenol, a synthetic beta-adrenergic receptor agonist which controls peripheral vasoconstriction, bronchodilation and increased cardiac rate, contractility and output.

SNC80: 4-[("R)-α-((2S,5R)-4-allyl-2,5-dimethyl-1-piperazinyl)-3-methoxybenzyl]-N,N-diethylbenzamide. An agonist of the delta-opioid receptor that possesses anti-nociceptive action.

PAF: platelet-activating factor; a hormone that regulated platelet aggregation It is an agonist of the PAF receptor.

hRANTES: human RANTES (regulated upon activation, normal T cell expressed and secreted) is a chemoattractant for monocytes and T cells. It is an agonist of the chemokine CCR5 receptor.

Wnt5a: Ligand for members of the frizzled family of seven transmembrane receptors.

IGF1: insulin-like growth factor 1 (also known as somatomedin C), a hormone homologous to proinsulin.

TGF-β1: Transforming Growth Factor-beta1, a multifunctional peptide that controls proliferation, differentiation, and other functions in many cell types. Many cells synthesize TGF-beta 1 and essentially all of them have specific receptors for this peptide. TGF-beta 1 regulates the actions of many other peptide growth factors and determines a positive or negative direction of their effects.

Specific Inverse Agonist

SR121463: SR121463 is a selective, orally active, non-peptide antagonist of vasopressin (AVP) V2 receptors with powerful aquaretic properties in various animal species and humans. SR121463 also behaves as an inverse agonist in cells expressing constitutively active human V2 receptor.

Specific Receptors $\beta_2$-AR: beta-2 adrenergic receptor

Frizzled 4 (Fz4): a seven transmembrane receptor that selectively recognizes hormones of the Wnt family.

V2R: V2-vasopressin receptor

V1aR: V1a vasopressin receptor

δ-OR: δ-opioid receptor

PAFR: platelet-activating factor receptor

CCR5: CC chemokine receptor type 5

AT1aR: angiotensin receptor type 1a

Methods

Expression vectors. Plasmids encoding Flag-AT1aR, CCR5 (Pleskoff et al, 1997) and Myc-PAFR (Marrache et al, 2002) were provided by S. Meloche, N. Heveker and S. Chemtob, respectively (Université de Montréal, Québec, Canada). and WT β-arr2 was a generous gift from S. Marullo (Institut Cochin, Paris). Myc-V2R and HA-V1aR (Terrillon et al, 2003), Myc-$\beta_2$-AR (Hebert et al, 1996), Myc-δ-OR (Petaja-Repo et al, 2002), V2R-GFP (Charest & Bouvier, 2003), $\beta_2$-AR-GFP (Mercier et al, 2002), β-arr2-YFP (Angers et al, 2000) and Luc-β-arr2 (Perroy et al, 2003) have been described previously. Luc-β-arr-YFP was generated by subcloning the coding sequence of enhanced YFP in-frame at the C terminus of β-arr2 in pcDNA3.1-Luc-β-arr2, yielding Luc-βarr-YFP with flexible spacers of 23 aa between Luc and β-arr, and 10 aa between β-arr and YFP. Mutation of arginine 169 into glutamate in Luc-β-arr (R169E)-YFP was generated by PCR site-directed mutagenesis using Luc-β-arr-YFP. It should be noted that while the construct described here is specific for Luc-β-arr-YFP, a construct leading to the production of a YFP-β-arr-Luc biosensor is feasible. Moreover, the resulting biosensor, YFP-β-arr-Luc, would be expected to function in the same manner as Luc-β-arr-YFP. Similarly, DNA constructs may be devised for the specific expression of Luc-β-arr-GFP, GFP-β-arr-Luc biosensors, and variants thereof.

Cell culture. Human embryonic kidney 293 (HEK293) cells and simian kidney fibroblast (COS) cells were maintained as described previously (Charest & Bouvier, 2003). Cells were transfected with the indicated plasmids using the calcium phosphate precipitation method (Sambrook et al, 1989) or the FuGENE 6 transfection reagent (Roche Applied Science, Laval, Canada) according to the manufacturer's protocol. The experiments were performed 48 h after transfection.

Fluorescence microscopy. To detect Myc-$\beta_2$-AR and Myc-V2R, cells were incubated with anti-Myc 9E10 monoclonal antibody (ascite fluid from our core facility) for 1 h at 4° C. and then treated with the appropriate agonist (Sigma, Oakville, Canada) for 2 or 30 min at 37° C. Cells were then fixed and permeabilized before adding Texas-red-conjugated secondary antibody (Santa Cruz Biotechnology Inc., Santa Cruz, Calif., USA). The samples were analysed by confocal laser-scanning microscopy using a Leica TCS SP1. Measurements were as follows: YFP (green),$\lambda_{ex}$=488 nm, $\lambda_{em}$=540/25 nm; Texas red (red), $\lambda_{ex}$=568 nm, $\lambda_{em}$=610/30 nm.

BRET assays. Assessment of β-arr recruitment in BRET was performed as described previously (Charest & Bouvier, 2003). Briefly, cells were distributed in 96-well microplates (Corning, Corning, USA) and incubated with or without agonist for the indicated time at 25° C. The appropriate Luc substrate was added to a final concentration of 5 mM, either simultaneously with the agonist (time course) or following agonist treatment (single measurement or dose dependency), and readings were collected using a Multilabel Reader Mithras LB 940 (Berthold Technologies, Bad Wildbad, Germany). To detect BRET1 between Luc and YFP, coelenterazine h (Molecular Probes, Burlington, Canada) was used as substrate and light emission was detected at approximately 460-500 nm (Luc) and approximately 510-550 nm (YFP), whereas for BRET2 detection (Luc and GFP), DeepBlueC™ coelenterazine (Perkin-Elmer, Wellesley, Mass., USA) and filters at approximately 330-470 nm (Luc) and approximately 495-535 nm (GFP2) were used. (Broadly speaking, ranges for the detection of light emission for BRET1 are approximately 440-510 nm (Luc) and 510-570 nm (YFP), while those for BRET2 are approximately 320-490 nm (Luc) and 490-550 nm (GFP)). The BRET signal was determined by calculating the ratio of the light emitted by the fluorescent acceptor and the light emitted by Luc. The values were corrected by subtracting the background BRET signals detected when Luc-β-arr was expressed alone. Expression levels of the different receptors transfected were verified by enzyme-linked immunosorbent assay (ELISA) (Charest & Bouvier, 2003).

Receptor endocytosis assay. Receptor endocytosis was measured by ELISA as described previously (Charest & Bouvier, 2003).

Results

Double-Brilliance β-Arr

Inspired by previous reports of intramolecular fluorescence resonance energy transfer (FRET)-based biosensors (Zhang et al, 2002) showing that resonance energy transfer (RET) is sensitive to changes in the relative positions of the donor and acceptor molecules, the feasibility of monitoring whether conformational changes of β-arr using an intramolecular BRET approach was assessed. A double-brilliance β-arr was engineered in which Luc was fused to the N terminus of β-arr2 and YFP to its C terminus, yielding Luc-β-arr-YFP (FIG. 1). To test the functionality of Luc-β-arr-YFP, the ability of this molecule to be recruited to agonist-stimulated class A (receptors interacting transiently with βarr) $\beta_2$-adrenergic receptor ($\beta_2$-AR) and class B (receptors interacting stably with βarr) V2 vasopressin receptor (V2R) by fluorescence microscopy was determined. As shown in FIG. 2A, agonist stimulation led to rapid translocation of Luc-β-arr-YFP to the plasma membrane, colocalizing with Myc-tagged $\beta_2$-AR and V2R (Myc-$\beta_2$-AR; Myc-V2R). The patterns of Luc-β-arr-YFP interaction were consistent with those observed for class A (transient β-arr interaction) and B (stable β-arr association) receptors in similar experiments using a β-arr-green fluorescent protein (GFP) conjugate (Oakley et al, 2000). Indeed, whereas Luc-β-arr-YFP was recruited to both $\beta_2$-AR and V2R after 2 min of stimulation, it returned to the cytoplasm after 30 min in Myc-$\beta_2$-AR-expressing cells but remained colocalized with Myc-V2R in endocytic vesicles.

Figure 2C:
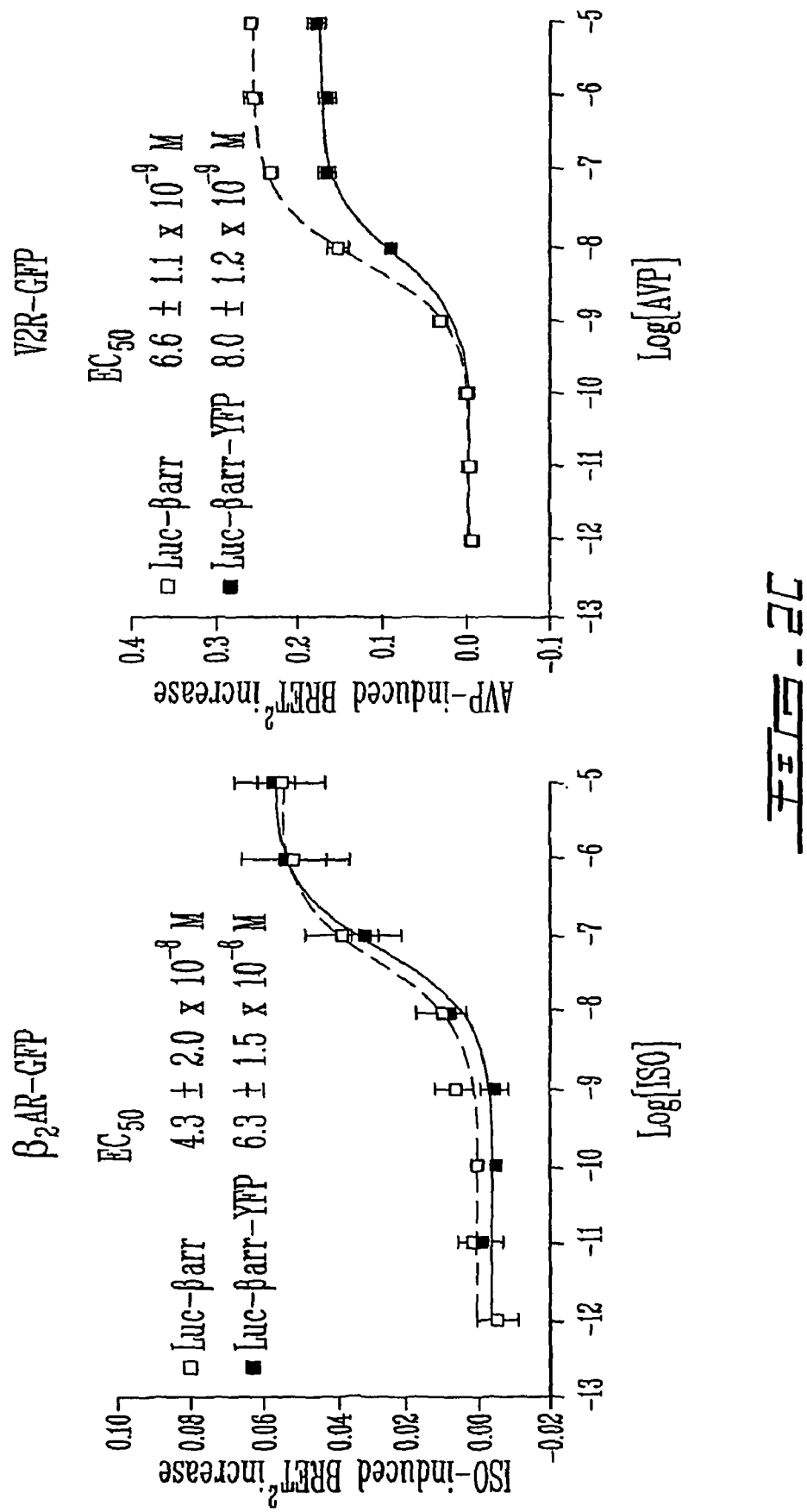
FIG. 2: Functionality of double-brilliance β-arr. HEK293 (A-C) or COS (D) cells were transiently transfected with the indicated plasmids. (A) Cells incubated or not in the presence of saturating concentrations of specific agonists ($β_2$-AR, 10 mM isoproterenol (ISO); V2R, 1 mM arginine vasopressin (AVP)). Localization of Luc-β-arr-YFP and Myc-tagged receptors was analysed by confocal fluorescence microscopy. (B) Agonist-induced recruitment of β-arr measured using intermolecular BRET2. $t_{1/2}$=half-time of maximal β-arr recruitment. (C) Dose-dependent recruitment of β-arr to the receptors measured in intermolecular BRET2 following 2 min stimulation with the agonist. $EC_{50}$=concentration of agonist producing half-maximal β-arr recruitment. (D) Cells treated or not for 15 min with the specific agonists at 37° C. and cell-surface receptor levels measured by enzyme-linked immunosorbent assay (ELISA). Receptor endocytosis is defined as the loss of cell-surface immunoreactivity and is expressed as a percentage of total immunoreactivity measured under basal conditions. Expression levels of β-arr were controlled using western blot (data not shown). Data are the mean±s.e.m. of at least three independent experiments. *$P<0.05$ between treatment and each individual control condition. Mock, nontransfected cells.
Figure 20:
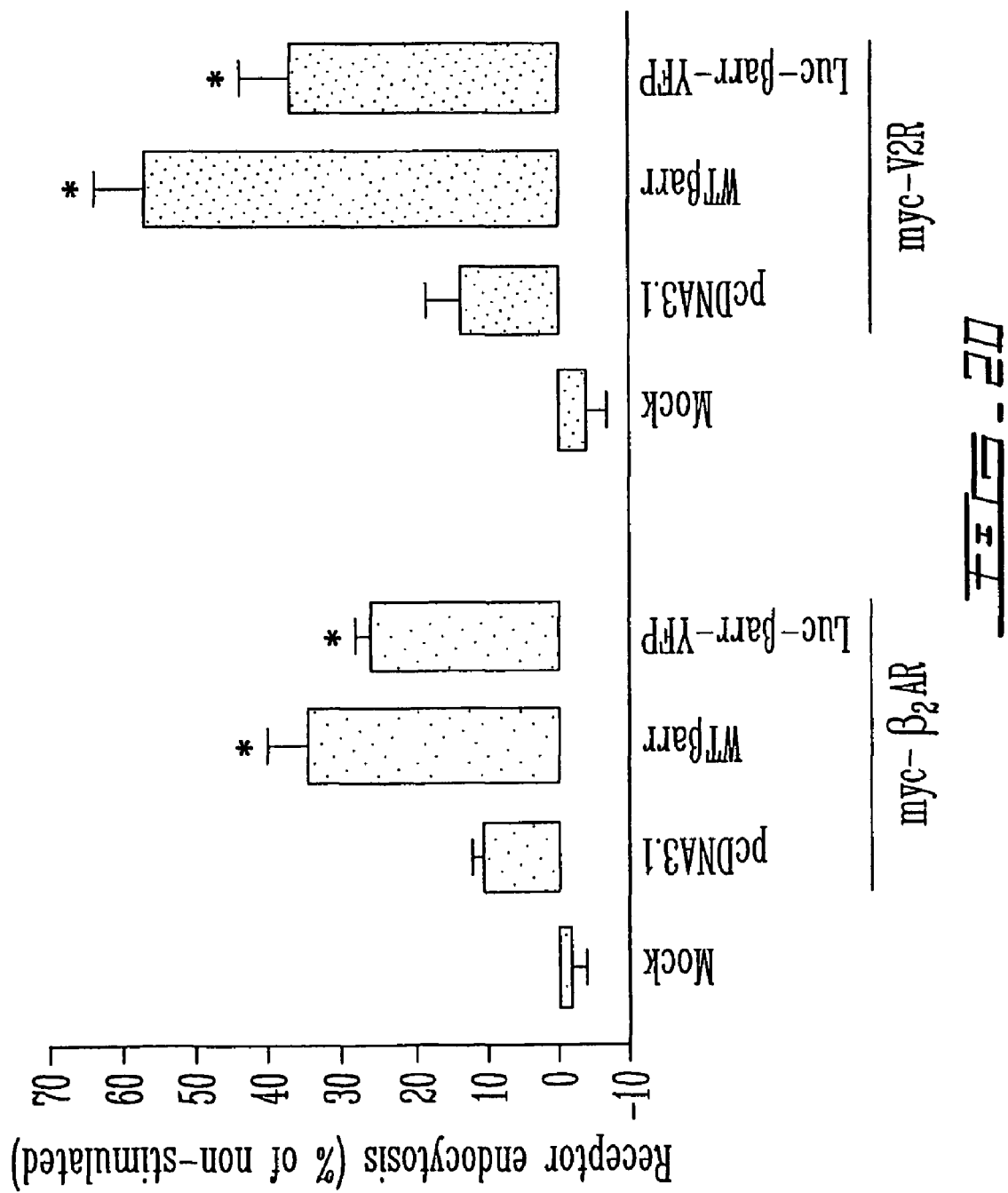

To quantitatively assess the recruitment of Luc-β-arr-YFP to agonist-activated GPCRs, an intermolecular BRET2 assay that takes advantage of the different spectral properties of Luc substrates that allow energy transfer to different fluorescent acceptors (Milligan, 2004) was used. Luc-β-arr-YFP was transiently coexpressed with the receptors, and the agonist-induced BRET2 between Luc-β-arr-YFP and either $\beta_2$-AR-GFP or V2R-GFP was measured in the presence of DeepBlueC™ coelenterazine, allowing transfer of energy to GFP. As shown in FIG. 2, agonist stimulation promoted a time-dependent (FIG. 2B) and dose-dependent (FIG. 2C) increase in BRET2, reflecting the recruitment of Luc-β-arr-YFP to the receptors. Similar kinetics and $EC_{50}$ were obtained for the recruitment of both Luc-β-arr-YFP and Luc-β-arr, indicating that double-brilliance β-arr is as efficiently recruited to the receptors as the singly conjugated construct. It should be noted that, although the maximum agonist-promoted BRET increase observed with the class A $\beta_2$-AR is less than that observed with class B V2R, the stability of the signals was similar, indicating that the signal observed with $\beta_2$-AR reflects a steady state corresponding to constant association and dissociation of β-arr from the activated receptors.

To assess the biological activity of Luc-β-arr-YFP, its capacity to promote receptor endocytosis in COS cells, which express low endogenous levels of β-arr, was tested. As shown in FIG. 2D, agonist-promoted $\beta_2$-AR and V2R endocytosis was considerably increased when overexpressing Luc-β-arr-YFP. Even though this increase in receptor endocytosis was not as pronounced as that obtained by the overexpression of wild-type (WT) β-arr, it suggests that Luc-β-arr-YFP retains significant biological activity.

Agonist-Induced Conformational Changes of β-Arr

Figure 3A:
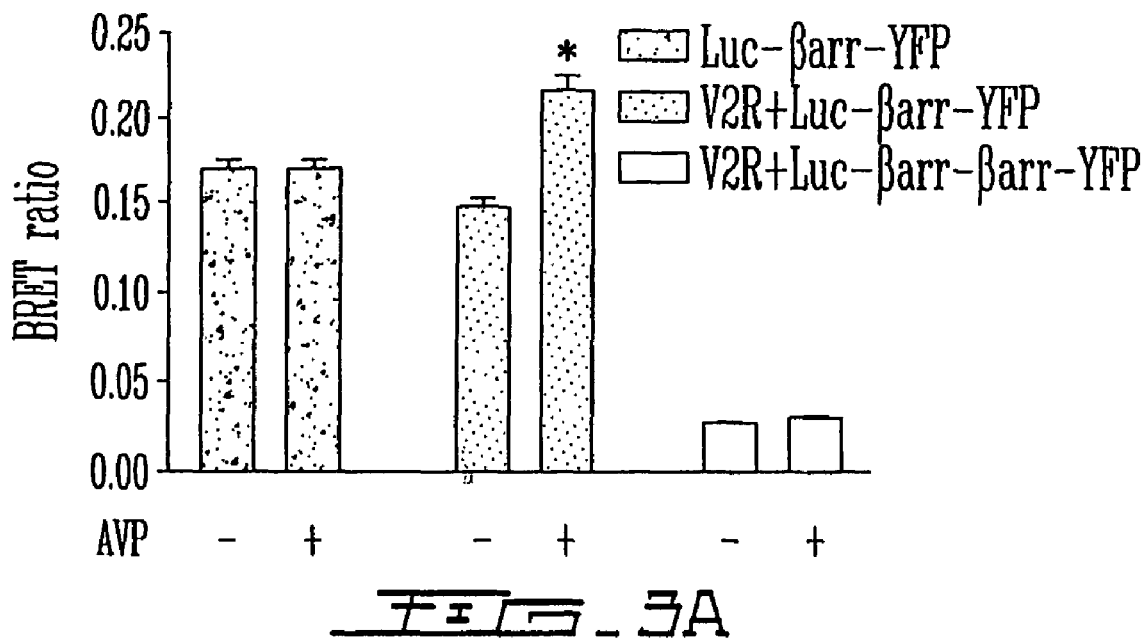
FIG. 3: AVP-induced conformational change of β-arr monitored by intramolecular BRET1. HEK293 cells were transfected with the indicated plasmids and BRET was measured at 25° C. in the presence of coelenterazine h. (A) Specificity of agonist-induced β-arr intramolecular BRET1. (B) Real-time BRET measurements of the agonist-induced β-arr conformational change. $t_{1/2}$=half-time of maximal conformational change of β-arr. (C) Dose-dependent agonist-promoted increase of β-arr intramolecular BRET1. Cells were stimulated with increasing concentrations of AVP for 4 min. $EC_{50}$=concentration of AVP producing half-maximal conformational change of β-arr. Data are the mean±s.e.m. of at least three independent experiments. *$P<0.01$ between treated and control condition.

To assess whether Luc-β-arr-YFP could be used to monitor the conformational rearrangement of β-arr upon receptor activation, the construct was expressed with and without V2R, and BRET was measured in the presence of coelenterazine h, allowing transfer of energy to YFP. As shown in FIG. 3A, an important basal BRET signal could be measured in cells transfected with Luc-β-arr-YFP, reflecting the proximity of the energy donor and acceptor in the construct. Arginine vasopressin (AVP) stimulation of cells coexpressing V2R led to a significant increase in BRET, suggesting movement of Luc and YFP relative to each other. To rule out the possibility that this increased signal results from intermolecular BRET between individual Luc-β-arr-YFP molecules brought together through oligomerization (Hirsch et al, 1999) or clustering at the plasma membrane, the occurrence of BRET in cells transiently expressing Luc-β-arr and β-arr-YFP was determined. In transfection conditions leading to equivalent fluorescence and luminescence levels as those obtained in Luc-β-arr-YFP-expressing cells, coexpression of Luc-β-arr and β-arr-YFP led to the detection of only a marginal basal BRET that could not be modulated by V2R stimulation (FIG. 3A). This observation demonstrates that the AVP-induced increase in BRET signal observed in cells transfected with Luc-β-arr-YFP results from a change in intramolecular BRET. As variations in RET can reflect changes in both the distance and orientation between the energy donor and acceptor molecules (Andrews & Demidov, 1999), the observed agonist-promoted increase in the Luc-β-arr-YFP intramolecular BRET could indicate that the N terminus and C terminus are either brought closer or are in a more permissive BRET orientation following activation.

Figure 3B:
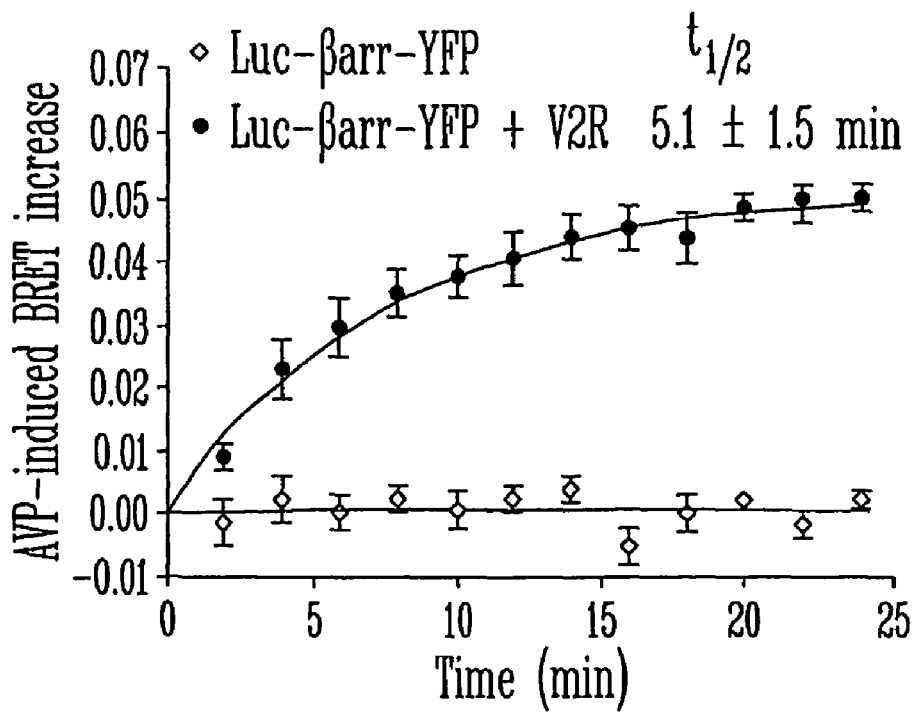

To further characterize the agonist-induced change in the conformation of β-arr, the kinetics and dose dependency of AVP-mediated BRET increase were assessed. Real-time BRET measurements show a time-dependent AVP-induced conformational change of β-arr, with half-time of maximal BRET increase ($t_{1/2}$) of 5.1±1.5 min (FIG. 3B). The kinetics are significantly slower (P<0.02) than that of the AVP-induced recruitment of β-arr ($t_{1/2}$=0.8±0.2 min; FIG. 2B, right panel), suggesting that the conformational change observed in Luc-β-arr-YFP occurs after its initial recruitment to the activated V2R. The difference in kinetics cannot result from inter-experimental variations because similar results were obtained when the two events were measured in the same cell population expressing V2R-GFP and Luc-β-arr-YFP (data not shown). Despite the difference in kinetics, the efficacy of AVP to induce a conformational change in Luc-β-arr-YFP (FIG. 3C) was similar to that observed for β-arr recruitment (FIG. 2C, right panel), indicating that these two events are directly linked and reflect the binding affinity of V2R for AVP (KD~$1\times10^{-9}$ M).

The observed kinetic lag between β-arr recruitment and its conformational change could be consistent with the proposal that inactive β-arr is first recruited to the activated GPCR where its interaction with the GRK-phosphorylated residues subsequently induces the release of its C-tail (Gurevich & Gurevich, 2003). Alternatively, such a lag could indicate that the intramolecular BRET changes observed with Luc-β-arr-YFP result from the subsequent recruitment of β-arr-interacting proteins (e.g. clathrin and AP2 or signalling proteins such as c-Src, Raf1, ERK1/2, ASK1 and JNK3) to the receptor-bound β-arr (Lefkowitz & Whalen, 2004). Interestingly, a β-arr (R169E) mutant shown to bind to GPCRs in a phosphorylation-independent manner, probably as a result of a constitutively open conformation (Kovoor et al, 1999) resulted, when inserted between Luc and YFP (Luc-β-arr(R169E)-YFP), in basal and AVP-stimulated BRET signals similar to those observed with WT Luc-β-arr-YFP (FIG. 4). This indicates that the engagement of βarr by the activated receptor can be detected by the double brilliance βarr independently of the phosphorylation state of the receptor.

A General Biosensor to Monitor GPCR Activity

Figure 5A:
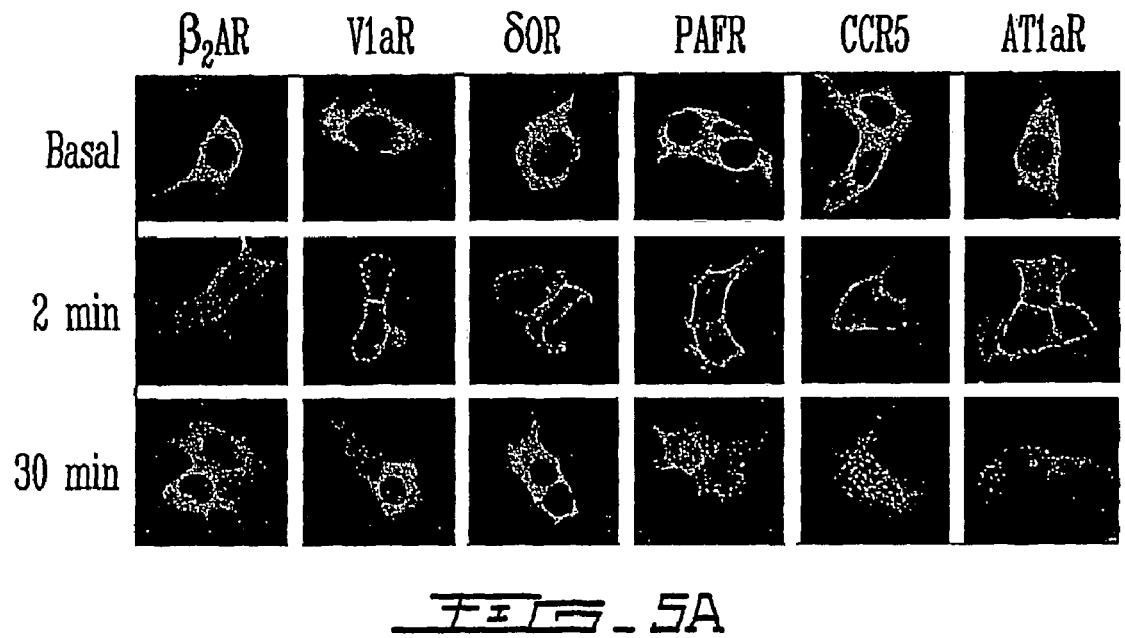
FIG. 5: Double-brilliance β-arr monitors the activation of many GPCRS. HEK293 cells were transfected with Luc-β-arr-YFP and either pcDNA3.1 or plasmids encoding the indicated receptors. (A) Agonist-induced translocation of Luc-β-arr-YFP measured following treatment with 1 mM of the specific agonists ($β_2$-AR, ISO; V1aR, AVP; δ-OR, SNC80; PAFR, PAF; CCR5, hRANTES; AT1aR, angiotensin II). (B) Agonist-induced conformational change of Luc-β-arr-YFP measured following 10 min stimulation with the specific agonists mentioned in (A). BRET1 was measured using a Multilabel Reader Mithras LB 940 (Berthold Technologies). The BRET signal was determined by calculating the ratio of the light emitted by YFP over the light emitted by Luc following the addition of coelenterazine h. Data are the mean±s.e.m. of three independent experiments. *$P<0.05$ between treatment and each individual control condition.
Figure 5B:
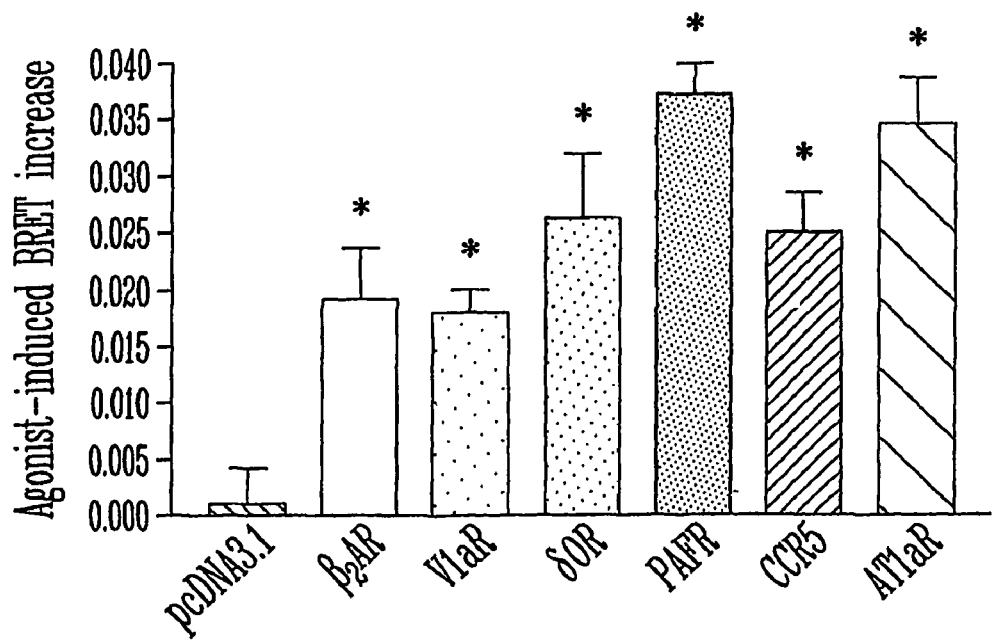

To assess whether Luc-β-arr-YFP could be used as a general GPCR activity sensor, a determination of whether its agonist-induced conformational change could be promoted by other receptors was made, particularly those of class A, which are believed to interact only transiently with β-arr. Recruitment of Luc-β-arr-YFP and agonist promoted intramolecular BRET were assessed in cells coexpressing different receptors of class A ($\beta_2$-AR, V1 vasopressin receptor (V1aR), d-opioid receptor (δ-OR)) and class B (platelet-activating factor receptor (PAFR), CC chemokine receptor type 5 (CCR5), angiotensin receptor type 1a (AT1aR)). As shown in FIG. 5A, agonist stimulation efficiently induced the recruitment of Luc-β-arr-YFP to the plasma membrane, with the expected interaction patterns for all class A (transient) and class B (stable) receptors. In all cases, activation of Luc-β-arr-YFP mediated by class A and B receptors was accompanied by a significant increase in BRET (FIG. 5B). Interestingly, although the kinetics and stability of the BRET increase were found to be similar for receptors of class A and B (data not shown), a tendency of class A receptors to induce smaller BRET increases was observed. As previously noted when comparing the BRET-detected recruitment of β-arr to class A $\beta_2$-AR and class B V2R (FIG. 2B), this probably indicates that the BRET assays provide a steady-state signal reflecting continuous rounds of association-dissociation cycles. In any case, these results suggest that Luc-β-arr-YFP can be used as a general biosensor to monitor GPCR activity and that the interaction can be monitored for extended periods of time making it compatible with its use in high through put screening assays that request long lived signals. When compared with the intermolecular BRET-based β-arr recruitment assays (Angers et al, 2000; Bertrand et al, 2002), double-brilliance β-arr avoids the difficulty of expressing the appropriate ratio of energy donor and acceptor constructs and allows the study of unmodified GPCRs. The interaction of β-arr with the GRK-phosphorylated GPCRs is thought to induce the release of β-arr's C-tail and the opening of its structure (Gurevich and Gurevich 2003), subsequently leading to the recruitment of βarrestin-interacting proteins (Lefkowitz and Whalen 2004).

To assess if the conformational change of β-arr detected with the double brilliance β-arr could also be detected using βarr mutants believed to be constitutively in the open state, assessment was made of the agonist-promoted BRET signal of two other β-arr mutants (β-arr(3A): I387A, V388A, F389A; β-arr (IV): I387A, V388A), inserted between Luc and YFP (Luc-βarr(3A)-YFP and Luc-βarr(IV)-YFP). These mutant β-arrs are believed to be constitutively active due to the disruption of the polar core keeping βarrestin in a closed and inactive conformation (Gurevich 1998). As shown in FIG. 6, while the basal BRET signal observed with each Luc-β-arr-YFP constitutively active mutant (Luc-βarr(3A)-YFP and Luc-βarr(IV)-YFP) was found to be similar to that of wild-type Luc-βarr-YFP, the agonist-induced BRET increase was significantly reduced by the mutations (FIG. 6, inset).

In addition to agonists, the activity of ligands with inverse agonist efficacy towards specific signalling pathways can be detected by the double brilliance β-arr. As shown in FIG. 7, the V2R inverse agonist SR121463 that inhibits cyclic AMP production can promote an increase in the BRET signal in cells co-expressing wild type V2R and Luc-β-arr-YFP.

Figure 8:
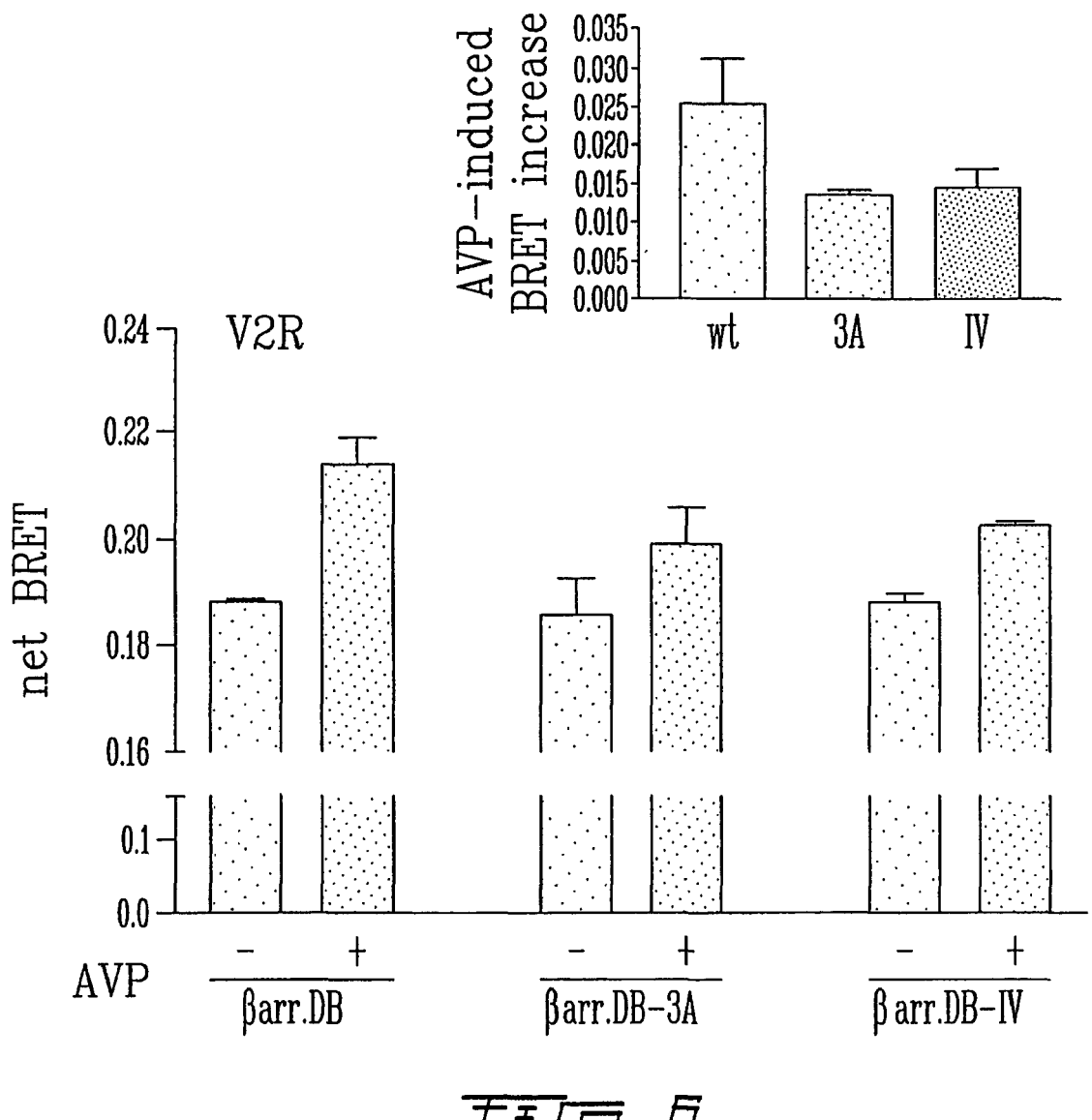
FIG. 8: βarrestin-dependant endocytosis beyond GPCRs. A) Endocytosis of the receptor Frizzled 4 (Fz4) stimulated by Wnt5a is orchestrated by βarrestin 2, in a manner that is dependent upon the phosphorylation of the adaptor protein Dishevelled 2 (Dvl2) by protein kinase C (PKC). B) Endocytosis of the RII and RIII receptor subtypes of TGF-β1 is orchestrated by βarrestin 2, and facilitated by the phosphorylation of RIII by RII. C) Endocytosis of the IGF1 receptor is orchestrated by βarrestin. (Modified from Lefkowitz & Whalen, 2004.)

Double brilliance β-arr may also prove to be an effective tool in the study of the increasingly diverse roles played by β-arr, such as its involvement with receptors other than GPCRs and diverse signaling molecules in different systems (FIG. 8). A list of some of the proteins that have been shown to interact with βarr and which activity could be monitored by double brilliance β-arr is presented in Table 1. The spectrum of receptors capable of utilizing β-arr for endocytosis via clathrin binding sites has significantly increased (Lefkowitz and Whalen 2004). For example, β-arr appears to be required for engulfing Frizzled-4, an atypical seven-transmembrane domain receptor, through interaction with the adaptor protein Dishevelled-2 phosphorylated by PKC (Chen et al. 2003a); for the endocytosis of receptors with serine/threonine kinase activity such as the transforming growth factor β receptor (TGF-βR), in a manner dependent on the phosphorylation of RIII by RII (Chen et al. 2003b); as well as for the endocytosis of the IGF1 receptor, in a manner that is independent from its phosphorylation (Dalle et al. 2001). This indicates that the βarr double brillance could be a general biosensor of the activity of many distinct receptors and signalling molecules.

| List of proteins capable of interacting with β-arrestin | | |
|---|---|---|
| Binding Protein | β-arrestin isoform | Type of protein |
| Clathrin | β-arr 1, 2 | trafficking |
| AP2 | β-arr 1, 2 | trafficking |
| NSF | β-arr 1 | trafficking |
| ARF6 | β-arr 2, 1 | Small G/GEFs |
| ARNO | β-arr 2 | Small G/GEFs |
| Ral-GDS | β-arr 1, 2 | Small G/GEFs |
| RhoA | β-arr 1 | Small G/GEFs |
| MAPK cascade components: | | Signalling |
| ASK1 | β-arr 1, 2 | |
| c-Raf-1 | β-arr 1, 2 | |
| JNK3 | β-arr 2, 1 | |
| ERK2 | β-arr 1, 2 | |
| Nonreceptor tyrosine kinases: | | signalling |
| c-Src | β-arr 1, 2 | |
| Yes | β-arr 1 | |
| Hck | β-arr 1 | |
| Fgr | β-arr 1 | |
| Others: | | signalling |
| Mdm2 | β-arr 1, 2 | |
| IκBα | β-arr 1, 2 | |
| PDE4D family | β-arr 1, 2 | |
| Dishevelled | β-arr 1, 2 | |
| PP2A | β-arr 1 | |

(Lefkowitz & Shenoy, 2005)

Since the fluorescent energy transfer of the invention is based on stimulatory principles such as BRET, a biosensor as described herein based on FRET instead of BRET would also be expected to function well and is included within the scope of the present invention.

In summary, the above is believed to be the first real-time monitoring of agonist-promoted conformational changes of β-arr in living cells using a double-brilliance β-arr intramolecular BRET-based biosensor. The conformational rearrangement of the β-arr molecule and its interaction with other proteins reflects its transition from an inactive state to a biologically active state that follows its initial recruitment to activated GPCRs and involves the relative movement of the C-tail of β-arr towards its N terminus (FIG. 1). As most GPCRs recruit β-arr in an agonist-dependent fashion, double-brilliance β-arr could represent a general tool to probe receptor activity that could be used advantageously in large-scale screening campaigns aimed at identifying GPCR ligands for other classes of receptors and signalling molecules. In conclusion, double brilliance β-arr represents the first intramolecular BRET-based biosensor that allows the monitoring of protein conformational changes. This should lead the way to the development of similar tools to study other proteins believed to undergo significant conformational rearrangement linked to their function.

Although the present invention has been described by way of specific embodiments and examples thereof, with a particular focus on G protein-coupled receptors, it should be noted that it will be apparent to persons skilled in the art that modifications may be applied to the present particular embodiment without departing from the scope of the present invention.

LIST OF REFERENCES

1. Andrews D L, Demidov A A (1999) Resonance Energy Transfer. Chichester, UK: Wiley
2. Angers S, Salahpour A, Joly E, Hilairet S, Chelsky D, Dennis M, Bouvier M (2000) Detection of β₂-adrenergic receptor dimerization in living cells using bioluminescence resonance energy transfer (BRET). Proc Natl Acad Sci USA 97: 3684-3689
3. Azzi M, Charest P G, Angers S, Rousseau G, Kohout T, Bouvier M, Pineyro G (2003) β-Arrestin-mediated activation of MAPK by inverse agonists reveals distinct active conformations for G protein-coupled receptors. PNAS 100: 11406-11411
4. Bertrand L, Parent S, Caron M, Legault M, Joly E, Angers S, Bouvier M, Brown M, Houle B, Menard L (2002) The BRET2/arrestin assay in stable recombinant cells: a platform to screen for compounds that interact with G protein-coupled receptors (GPCRs). J Receptor Signal Transduction Res 22: 533-541
5. Charest P G, Bouvier M (2003) Palmitoylation of the V2 vasopressin receptor carboxyl tail enhances β-arrestin recruitment leading to efficient receptor endocytosis and ERK1/2 activation. J Biol Chem 278: 41541-41551
6. Chen W, Kirkbride K C, How T, Nelson C D, Mo J, Frederick J P, Wang X F, Lefkowitz R J, Blobe G C (2003) Beta-arrestin 2 mediates endocytosis to type III TFG-beta receptor and down-regulation of its signalling. Science 301 (5638): 1394-1397
7. Dalle S, Ricketts W, Imamura T. Vollenweider P. Olefsky J M (2001) Insulin and insulin-like growth factor I receptors utilize different G protein signalling components. J Biol Chem 276 (19): 15688-15695
8. Gurevich V V, Benovic J L (1993) Visual arrestin interaction with rhodopsin. Sequential multisite binding ensures strict selectivity toward lightactivated phosphorylated rhodopsin. J Biol Chem 268: 11628-11638
9. Gurevich V, Gurevich E V (2003) The new face of active receptor bound arrestin attracts new partners. Structure (Camb) 11: 1037-1042

10. Han M, Gurevich V, Vishnivetskiy S A, Sigler P B, Schubert C (2001) Crystal structure of β-arrestin at 1.9 A°: possible mechanism of receptor binding and membrane translocation. Structure (Camb) 9: 869-880
11. Hebert T E, Moffett S, Morello J P, Loisel T P, Bichet D G, Barret C, Bouvier M (1996) A peptide derived from a $\beta_2$-adrenergic receptor transmembrane domain inhibits both receptor dimerization and activation. J Biol Chem 271: 16384-16392
12. Hirsch J A, Schubert C, Gurevich V, Sigler P B (1999) The 2.8 A° crystal structure of visual arrestin: a model for arrestin's regulation. Cell 97: 257-269
13. Kovoor A, Celver J, Abdryashitov R I, Chavkin C, Gurevich V V (1999) Targeted construction of phosphorylation-independent β-arrestin mutants with constitutive activity in cells. J Biol Chem 274: 6831-6834
14. Lefkowitz R J, Whalen E J (2004) β-arrestins: traffic cops of cell signalling. Curr Opin Cell Biol 16: 162-168
15. Lefkowitz R J, Shenoy S K (2005) Transduction of Receptor Signals by β-arrestins. Science 308: 512-517
16. Lin F T, Miller W E, Luttrell L M, Lefkowitz R J (1999) Feedback regulation of β-arrestin1 function by extracellular signal-regulated kinases. J Biol Chem 274: 15971-15974
17. Lin F T, Chen W, Shenoy S, Cong M, Exum S T, Lefkowitz R J (2002) Phosphorylation of β-arrestin2 regulates its function in internalization of b(2)-adrenergic receptors. Biochemistry 41: 10692-10699
18. Luttrell L M, Lefkowitz R J (2002) The role of β-arrestins in the termination and transduction of G-protein-coupled receptor signals. J Cell Sci 115: 455-465
19. Marrache A M et al (2002) Proinflammatory gene induction by plateletactivating factor mediated via its cognate nuclear receptor. J Immunol 169: 6474-6481
20. Mercier J F, Salahpour A, Angers S, Breit A, Bouvier M (2002) Quantitative assessment of b1- and $\beta_2$-adrenergic receptor homo- and heterodimerization by bioluminescence resonance energy transfer. J Biol Chem 277: 44925-44931
21. Milligan G (2004) Applications of bioluminescence- and fluorescence resonance energy transfer to drug discovery at G protein-coupled receptors. Eur J Pharm Sci 21: 397-405
22. Oakley R H, Laporte S A, Holt J A, Caron M G, Barak L S (2000) Differential affinities of visual arrestin, β-arrestin1, and β-arrestin2 for G proteincoupled receptors delineate two major classes of receptors. J Biol Chem 275: 17201-17210
23. Oakley R H, Laporte S A, Holt J A, Barak L S, Caron M G (2001) Molecular determinants underlying the formation of stable intracellular G proteincoupled receptor-β-arrestin complexes after receptor endocytosis. J Biol Chem 276: 19452-19460
24. Perroy J, Adam L, Qanbar R, Chenier S, Bouvier M (2003) Phosphorylationindependent desensitization of GABA(B) receptor by GRK4. EMBO J 22: 3816-3824
25. Petaja-Repo U E, Hogue M, Bhalla S, Laperriere A, Morello J P, Bouvier M (2002) Ligands act as pharmacological chaperones and increase the efficiency of d-opioid receptor maturation. EMBO J 21: 1628-1637
26. Pleskoff O, Treboute C, Brelot A, Heveker N, Seman M, Alizon M (1997) Identification of a chemokine receptor encoded by human cytomegalovirus as a cofactor for HIV-1 entry. Science 276: 1874-1878
27. Sambrook J, Fritsch E F, Maniatis T (1989) Molecular Cloning: A Laboratory Manual. New York: Cold Spring Harbor Laboratory Press
28. Terrillon S, Durroux T, Mouillac B, Breit A, Ayoub M A, Taulan M, Jockers R, Barberis C, Bouvier M (2003) Oxytocin and vasopressin V1a and V2 receptors form constitutive homo- and heterodimers during biosynthesis. Mol Endocrinol 17: 677-691
29. Vishnivetskiy S A, Hirsch J A, Velez M G, Gurevich Y V, Gurevich V V (2002) Transition of arrestin into the active receptor-binding state requires an extended interdomain hinge. J Biol Chem 277: 43961-43967
30. Xiao K, Shenoy S K, Nobles K, Lefkowitz R J (2004) Activation dependent conformational changes in β-arrestin 2. J Biol Chem 279: 55744-55753
31. Zhang J, Campbell R E, Ting A Y, Tsien R Y (2002) Creating new fluorescent probes for cell biology. Nat Rev Mol Cell Biol 3: 906-918

What is claimed is:

1. A bioluminescence resonance energy transfer (BRET) biosensor, said biosensor comprising a protein with affinity to receptors or signalling molecules, wherein said protein is comprised of a bioluminescent indicator fused to one end of Beta(β)-arrestin and a fluorescent indicator fused to the other end of Beta(β)-arrestin.

2. A biosensor as defined in claim 1, wherein said Beta(β)-arrestin is Beta(β)-arrestin-1 or Beta(β)-arrestin-2.

3. A biosensor as defined in claim 1, wherein said bioluminescent indicator is a protein or an enzyme.

4. A biosensor as defined in claim 3, wherein said bioluminescent indicator is luciferase.

5. A biosensor as defined in claim 4, wherein said bioluminescent indicator is *Renilla* luciferase.

6. A biosensor as defined in claim 1, wherein said fluorescent indicator is a fluorophore protein or an enzyme.

7. A biosensor as defined in claim 6, wherein said fluorophore protein is Yellow Fluorescent Protein, Green Fluorescent Protein-2 or a variant thereof.

8. A biosensor as defined in claim 1, wherein said bioluminescent indicator is luciferase and said fluorescent indicator is Yellow Fluorescent Protein, Green Fluorescent Protein-2, a variant of Yellow Fluorescent Protein, or a variant of Green Fluorescent Protein-2.

9. A biosensor as defined in claim 8, wherein said bioluminescent indicator is *Renilla* luciferase and said fluorescent indicator molecule is Yellow Fluorescent Protein.

10. A biosensor as defined in claim 8, wherein said bioluminescent indicator is *Renilla* luciferase and said fluorescent indicator is Green Fluorescent Protein-2.

11. A biosensor as defined in claim 9 which is selected from the group consisting of Luc-β-arr-YFP, YFP-βarr-Luc, Luc-β-arr(3A)-YFP, arr(IV)-YFP or Luc-βarr(R169E)-YFP.

12. A method for identifying an agonist or inverse agonist for a receptor or signalling molecule, said method comprising:
  incubating (i) cells co-expressing the receptor or signalling molecule and the biosensor defined in claim 1, with a potential agonist or inverse agonist, or (ii) an isolated receptor or signalling molecule and the biosensor as defined in claim 1, with a potential agonist or inverse agonist;
  adding a suitable substrate to detect bioluminescence resonance energy transfer (BRET) in said biosensor;
  detecting a BRET signal; and
  comparing the BRET signal with a BRET signal obtained under similar conditions in the absence of the potential agonist or inverse agonist, wherein the potential agonist or inverse agonist is identified as an agonist or inverse agonist if a change in BRET signal level is observed.

13. A method as defined in claim 12, wherein the bioluminescent indicator is luciferase and the fluorescent indicator is Yellow Fluorescent Protein, the suitable substrate is coelenterazine h and the BRET signal is evaluated by detecting light emissions at about 440-510 nm and at about 510-570 nm.

14. A method as defined in claim 12, wherein the bioluminescent indicator is luciferase and the fluorescent indicator is Green Fluorescent Protein-2, the suitable substrate is Deep-Blue™ and the BRET signal is evaluated by detecting light emissions at about 320-490 nm and at about 490-550 nm.

15. A method as defined in claim 12, wherein said receptor is a Frizzled protein receptor or a G protein-coupled receptor.

16. A method as defined in claim 15, wherein said receptor is chosen from the group consisting of Frizzled 4 (Fz4), $\beta_2$AR, V1 vasopressin receptor (V1aR), V2 vasopressin receptor (V2R), delta-opioid receptor ($\delta$OR), platelet-activating factor receptor (PAFR), CC chemokine receptor type 5 (CCR5), angiotensin receptor type 1a (AT1aR).

17. A method as defined in claim 12, wherein said receptor is chosen from the group consisting of tyrosine kinase, serine kinase, threonine kinase, such as insulin-like growth factor 1 receptor (IGFR) and Transforming Growth Factor-beta1 receptor (TGFR).

18. A method as defined in claim 12, wherein said signalling molecule is chosen from the group consisting of ARF6, ARNO, Ral-GDS, RhoA, ASK1, c-Raf-1, JNK3, ERK2, c-Src, Yes, Hck, Fgr, Mdm2, I$\kappa$B$\alpha$, PDE4D family, Disheveled and PP2A.

19. A method of identifying an antagonist or allosteric regulator for a receptor or signalling molecule, said method comprising:
    incubating cells co-expressing the receptor or signalling molecule and the biosensor defined in claim 1, with a potential antagonist or allosteric regulator in the presence of an agonist or inverse agonist, or (ii) an isolated receptor or signalling molecule and the biosensor as defined in claim 1, with a potential antagonist or allosteric regulator in the presence of an agonist or inverse agonist;
    adding a suitable substrate to detect bioluminescence resonance energy transfer (BRET) in said biosensor;
    detecting the BRET signal; and
    comparing said detected BRET signal with a BRET signal caused by the agonist or inverse agonist under similar conditions in the absence of the potential antagonist or allosteric regulator,
    wherein if said detected BRET signal is different, the potential antagonist or allosteric regulator is identified as an antagonist or allosteric regulator, and wherein if the detected BRET signal is increased, the potential antagonist or allosteric regulator may be further identified as an allosteric regulator rather than an antagonist.

20. A method as defined in claim 19, wherein the bioluminescent indicator is luciferase and the fluorescent indicator is Yellow Fluorescent Protein, the suitable substrate is coelenterazine h and the BRET signal is evaluated by detecting light emission at about 440-510 nm and at about 510-570 nm.

21. A method as defined in claim 19, wherein the bioluminescent indicator is luciferase and the fluorescent indicator is Green Fluorescent Protein, the suitable substrate is Deep-Blue™ and the BRET signal is evaluated by detecting light emission at about 320-490 nm and at about 490-550 nm.

22. A method as defined in claim 19, wherein said receptor is a Frizzled protein receptor or a G protein-coupled receptor.

23. A method as defined in claim 22, wherein said receptor is chosen from the group consisting of Frizzled 4 (Fz4), $\beta_2$AR, V1 vasopressin receptor (V1aR), V2 vasopressin receptor (V2R), delta-opioid receptor ($\delta$OR), platelet-activating factor receptor (PAFR), CC chemokine receptor type 5 (CCR5), angiotensin receptor type 1a (AT1 aR).

24. A method as defined in claim 19, wherein said receptor is chosen from the group consisting of tyrosine kinase, serine kinase, threonine kinase, such as insulin-like growth factor 1 receptor (IGFR) and Transforming Growth Factor-beta1 receptor (TGFR).

25. A method as defined in claim 19, wherein said signalling molecule is chosen from the group consisting of ARF6, ARNO, Ral-GDS, RhoA, ASK1, c-Raf-1, JNK3, ERK2, c-Src, Yes, Hck, Fgr, Mdm2, I$\kappa$B$\alpha$, PDE4D family, Disheveled and PP2A.

26. A biosensor chosen from the group consisting of YFP-$\beta$arr-Luc, Luc-$\beta$-arr(3A)-YFP, Luc-$\beta$-arr(IV)-YFP, Luc-$\beta$arr(R169E)-YFP and all other functional mutants of Luc-$\beta$-arr-YFP.

27. A cell line comprising a vector encoding a biosensor chosen from the group consisting of Luc-$\beta$-arr-YFP, YFP-$\beta$-arr-Luc, Luc-$\beta$-arr-GFP, GFP-$\beta$-arr-Luc, or a variant thereof.

\* \* \* \* \*